United States Patent [19]

Cohen et al.

[11] Patent Number: 5,161,553

[45] Date of Patent: Nov. 10, 1992

[54] PROCESS FOR SIMULTANEOUSLY WAVING AND COLORING HAIR

[75] Inventors: David Cohen, Milford; Leszek J. Wolfram, Stamford, both of Conn.

[73] Assignee: Clairol Incorporated, Stamford, Conn.

[21] Appl. No.: 909,445

[22] Filed: Sep. 19, 1986

[51] Int. Cl.$^5$ ............................................. A45D 7/04
[52] U.S. Cl. ...................................................... 132/205
[58] Field of Search ...................... 132/7, 205; 424/70

[56] References Cited

U.S. PATENT DOCUMENTS

| | | |
|---|---|---|
| 2,719,104 | 9/1955 | Westerberg . |
| 2,975,101 | 3/1961 | Charle et al. . |
| 3,173,842 | 3/1965 | Hervey et al. . |
| 3,215,605 | 11/1965 | Soloway . |
| 3,247,067 | 4/1966 | Miskel et al. . |
| 3,368,941 | 2/1968 | Boosen . |
| 3,396,736 | 8/1968 | Shansky . |
| 3,399,682 | 9/1968 | Isaji . |
| 3,399,683 | 9/1968 | Forbriger et al. . |
| 3,415,606 | 12/1968 | Randebrock . |
| 3,567,355 | 3/1971 | Boosen et al. . |
| 3,649,158 | 3/1972 | Kalopissis et al. . |
| 3,865,930 | 2/1975 | Abegg et al. . |
| 3,912,446 | 10/1975 | Zviak et al. . |
| 3,957,065 | 5/1976 | Busch et al. . |
| 3,966,397 | 6/1976 | Leon et al. . |
| 3,973,574 | 8/1976 | Minagawa et al. . |
| 4,149,848 | 4/1979 | Bugaut et al. . |
| 4,152,112 | 5/1979 | Bugaut et al. . |
| 4,277,244 | 7/1981 | Bugaut et al. . |
| 4,494,557 | 1/1985 | Nagel . |
| 4,566,875 | 1/1986 | Grollier et al. . |
| 4,630,621 | 12/1986 | Pontani . |

FOREIGN PATENT DOCUMENTS

| | | |
|---|---|---|
| 0166100 | 4/1985 | European Pat. Off. . |
| 3138142 | 4/1983 | Fed. Rep. of Germany . |
| 3543453 | 6/1987 | Fed. Rep. of Germany . |
| 53-96336 | 8/1978 | Japan . |
| 8703474 | 11/1986 | PCT Int'l Appl. . |

OTHER PUBLICATIONS

Poucher, Perfumes, Cosmetics and Soaps, vol. III—Modern Cosmetics (7th Edition 1979) pp. 93–105.
Balsam and Sagarin, Cosmetics Science and Technology, vol. 2, (2nd Edition 1972) pp. 224–229.
Chem. Abst., vol. 89, p. 364, 185,918 (1978).

*Primary Examiner*—Vincent Millin
*Attorney, Agent, or Firm*—Charles J. Zeller

[57] ABSTRACT

A process for simultaneously cold waving and coloring hair in which the neutralization of the hair waving composition is accomplished in two stages, the second stage of which involves the use of a neutralizing composition containing a hair dye.

1 Claim, No Drawings

PROCESS FOR SIMULTANEOUSLY WAVING AND COLORING HAIR

This invention relates to a process for simultaneously cold waving and coloring hair.

Hair waving and hair coloring are among the most complex and time consuming processes in today's hair care arsenal. As many women both color and wave their hair, there has been a frequently voiced need for a single process that would combine the two. As presently practiced, waving and coloring are somewhat incompatible. The hair coloring formulations are usually applied to dry hair in its natural configuration while waving is done on wet hair that is wrapped more or less tightly on the waving rods or rollers. Also, as the hair dyes can interact with the reducing ingredients of waving lotions, mixing the two at the onset of a combined process has a detrimental effect on both the color and the curl level. Immediate sequential treatments are undesirable because of potential scalp irritation when the hair coloring follows waving and the fear of high hair damage when the processes are reversed.

The current practice for cold waving hair generally involves rolling hair strands in a curler and then applying a solution of a reducing agent (e.g. ammonium thioglycolate or sodium or ammonium sulfite) to the hair to cleave the disulfide linkages in the hair keratin structure to soften the hair so as to make it possible to reform the hair into a desired shape. After a specified period of time allowed for shape re-arrangement the hair is rinsed. This step removes the excess of the reducing agent from hair, arrests the process of further cleavage and, in some degree, reverses the reaction which thus leads to limited bond rebuilding. The final step in hair waving is the "neutralization" process which aims at full restoration of cleaved disulfide bonds by means of oxidizing agents (usually a solution of $H_2O_2$). This is accomplished in two stages. First, half of the neutralizer is applied to hair while the latter is still wound on rods. After a few minutes, the rods (rollers) are removed and the rest of the neutralizing solution is worked into the now loose hair mass and left there for 2–5 minutes.

It has now been found that by adding dye components to the remaining solution of oxidizing agent and applying it to hair in the second stage of neutralization, an intense color can be produced on hair within the short time left for the final neutralization.

The degree of color intensity can be varied by changing the concentration of the dye additives. It is well known that, in many cases, a significant loss of color occurs upon waving. The process of this invention can thus be used as a color restorer, as well as obtaining a desired color change.

In the process of the present invention the dyes that may be incorporated in the "neutralizing" solution used in the second stage of neutralization may be any of a variety of types. For example, the dyes may constitute a system of oxidation dyes whose color is developed on the the hair through the aid of the oxidizing agent in the second stage "neutralizing" solution. Also, by way of example, the dyes might be of the direct dye type in which one or more direct dyes are contained in the second stage neutralizing solution to obtain the desired color in the dyeing operation. The only limitation on the character of the direct dye that may be utilized is that it should be one that is not significantly destroyed by the oxidizing agent in the second stage neutralizing solution.

There have been several suggestions in the prior art for the simultaneous waving and coloring of hair. Typical among these are those shown in U.S. Pat. Nos. 4,566,875; 3,399,682; 2,776,668; 3,415,606; 3,567,355, 3,966,397; 3,865,930 and 3,957,065. The processes disclosed in these patents are of a variety of types involving, for example, the pretreatment of hair with a reducing agent to facilitate the subsequent dyeing of the hair. However, none of these references teach the basic features of the present invention which entail subjecting the hair to a permanent waving solution containing a reducing agent, for sufficient time and at sufficient concentration to wave hair followed by a two-step neutralizing step in which the second step is affected by a neutralizing solution containing an oxidizing agent and a hair dye.

The hair waving composition that can be employed in the practice of the present invention may be any of the cold hair waving compositions that are well known to those skilled in this art. These generally constitute one or more reducing agents which are dissolved or distributed in liquid vehicle. Typical among the reducing agents that may be employed for the present purposes are the following: thioglycolic acid and salts thereof (e.g. ammonium, ethanolamine etc.), sulfites (sodium, potassium, ammonium), thioglycerol and its esters, etc.

The quantity of reducing agent that will be contained in the hair waving composition employed herein may vary somewhat and generally will be within the ranges commonly employed in this art. Usually this will amount to about 2% to about 15% by weight of reducing agent based on the total weight of the hair waving composition with the preferred range being from about 4% to about 10% on the same weight basis.

The liquid vehicle of the hair waving composition will usually be an aqueous vehicle in which the primary component will be water. In addition to the water and the reducing agent the hair waving composition may contain a variety of hair waving adjuvants that function to facilitate the preparation of the hair waving composition, ease of its application to the hair, improve its stability or its organoleptic qualities and condition the hair after waving. By way of illustrating the adjuvants that may be employed mention may be made of the following: surface active agents such as Laureth-23 or Nonoxynol-10 (both CTFA nomenclature) to lower the surface tension of the waving solution thus allowing for a better hair penetration; fragrance, conditioning agents such as cationic polymers or long chain quaternary ammonium compounds, etc.

The first stage neutralization step of the present invention may be carried out with the so called "neutralization" solutions well known in this art for the so called "hardening" of hair after treatment with the hair waving composition containing the reducing agent. This, as is commonly believed in this art, serves to reestablish at least in part some of the keratin disulfide linkages in the hair that are broken during the treatment with the reducing agent.

The first stage neutralization solution will contain one or more oxidizing agents which are compatible with the skin and hair at the concentration that these compositions are employed. A number of oxidizing agents are available that meet these criteria. These include such items as aqueous hydrogen peroxide, aqueous solutions of potassium or sodium bromate, salts of persulfuric acid and the like. The concentration of the oxidizing agent in the first stage neutralizing solution may vary over a range which will generally be from about 1% to about 15% by weight based on the total weight of the neutralization solution with the preferred range being from about 1.5% to about 12% on the same weight basis.

The oxidizing agent of choice for use in the first stage neutralization is hydrogen peroxide. This will generally constitute from about 1% to about 3% on a weight basis based on the total weight of the first stage neutralization solution with the optimum results being obtainable with a first stage neutralization solution containing from about 1.5% to about 2.5% on the same weight basis.

As is the case with the hair waving composition the principal component of the vehicle of the first stage neutralization solution will be water. In addition to the water the first stage neutralization solution may advantageously contain other adjuvants often found in such compositions. These include such materials as thickeners (e.g. cetyl alcohol, stearic acid amide) opacifier (Nonoxynol, -4, Nonoxynol-9), pH adjusters (phosphoric acid), etc.

The second stage neutralization solution will comprise essentially an oxidizing agent or agents and one or more hair dyes dissolved or distributed in a liquid vehicle. For the most part, and particularly in the case when the hair dyes employed are oxidation hair dyes or part of a system of oxidation hair dyes, the hair dyes will be added to the second stage neutralization solution just before use.

The oxidizing agents employed in the second stage neutralizing solution may be the same as that contained in the first stage neutralizing solution or it may be a different oxidizer. However, for convenience, the same oxidizing agent will be used for both the first and second stage neutralizing solutions.

The concentration of oxidizing agent in the second stage neutralizing solution will generally be about the same as the oxidizing agent in the first stage neutralizing solution. Usually this will amount to about 1% to about 6% by weight of oxidizing agent based on the total weight of the second stage neutralizing solution with the preferred range being from about 1% to about 4.5% on the same weight basis.

The oxidizing agent of choice in the second stage neutralizing solution will also be hydrogen peroxide. In this case the hydrogen peroxide will usually constitute from about 1% to about 3% by weight, based on the total weight of the second stage neutralization solution.

As indicated above after the hair has been subjected to a cold hair waving treatment with a composition containing a reducing agent, followed by a treatment with a first neutralizing solution, the hair is then treated with a second neutralizing solution that contains at least one hair dye. Since the hair dye will preferably be added to the second neutralizing solution just before use it may be best to express the concentration of the hair dye employed when it constitutes part of the second neutralizing solution. Furthermore, since one or more hair dyes may be employed to obtain a desired coloring of the hair, or the hair dyes may be used in conjunction with certain other compounds that serve to modify the color of the primary hair colors by a reaction therewith, it is useful to talk about hair dye systems in defining the concentration of the hair dyes. In this connection the term hair dye system is to be understood as encompassing to a single hair dye, a combination of hair dyes and a combination of hair dyes and hair dye color modifiers or couplers.

With the above in mind we can say that the hair dye system contained in the second stage neutralizating solution may constitute from about 0.1 to about 1% by weight, based on the total weight of the compositions. In the preferred practice of this invention the hair dye system will comprise about 0.1% to about 0.5% on the same weight basis.

Numerous types of hair dyes may be incorporated in the second stage neutralizing solution employed in the practice of the process of this invention. One type is the direct dyes that is characterized by the fact that dyes of this group directly dye hair and do not require additional reagents to develop its color. These direct dyes may be used singly or in combination, but they will most often be used in combination and blended to give natural appearing hair colors. In addition they may also be used in combination with an oxidation hair dye system when certain colors or effects are desired.

A multitude of direct hair dyes are known in the hair dye art that are useful for the present purposes. The only requirement is that the dye or dyes selected are stable toward the oxidizing agent that will be contained in the second stage neutralizing solution. By way of illustrating direct hair dyes that may form part of the second stage neutralizing solution the following may be mentioned: N-(2-hydroxyethyl)-2-nitro aniline;$N_1,N_4,N_4$-tris(2-hydroxyethyl)-2-nitro-p-phenylenedia mine; Disperse Black 9; Disperse Blue 1.

Another type of hair dye that may be contained in the second stage neutralizing solution utilized in the process of this invention is the so-called oxidation hair dyes which are characterized by the fact that the dyes of this group require an oxidizing agent to develop their color. The oxidation hair dye systems may comprise one or more of the so-called primary hair dye intermediates that produce color when oxidized with an oxidizing agent for example, hydrogen peroxide. The oxidation hair dye systems may also contain one or more color couplers or color modifiers. These, ordinarily, do not produce a color when oxidized alone. However, when oxidized in the presence of one or more primary hair dye intermediates they serve to modify the color that would ordinarily have been produced by the oxidation of these primary hair dye intermediates in the absence of such modifiers.

A large number of primary oxidation hair dye intermediates well known to those skilled in this art may be employed as part of the second stage neutralizing solution in the process of this invention. Illustrative of such primary oxidation hair dye intermediates are: paraphenylenediamine, paraaminophenol, N,N-bis(2-hydroxyethyl)-paraphenylenediamine sulfate.

Similarly, numerous oxidation hair dye couplers or modifiers are of common knowledge to those versed in the hair dye art that may be used along with the primary oxidation dye intermediates. To illustrate these mention may be made of resorcinol; 4-amino-2-hydroxytoluene; metaphenylenediamine, etc.

In the practice of the process of this invention the hair dye systems will usually be made up into hair dye liquid concentrates which are intended to be mixed with a solution of the oxidizing agent just before use in the second stage neutralization step. The concentration of the hair dye system in such liquid concentration may vary somewhat. Usually this will comprise from about 1% to about 8% by weight of hair dye on the same weight bases.

The vehicle for the hair dye concentrate will usually be a liquid vehicle and preferably an aqueous vehicle. In addition to water, these vehicles may contain a number of adjuvants that may facilitate the application of the hair dyes to the head, improve the dyeing properties of the concentrate, promote the stability of the concentrate or improve its organoleptic qualities. Such adjuvants are well known to those skilled in this art, and by way of example the following may be mentioned: solvents such as carbitol, isopropyl alcohol, glycerine; surfactants such as Igepal C0630, Triton X-15; viscosity modifiers such as oleic acid, and alkalizers such as ammonium hydroxide, monoethanolamine etc.

The pH of the dye concentrate may vary somewhat. Since it is advantageous to apply the hair dye to the head from an alkaline medium the pH of the concentrate will ordinarily be in the range of from about 8.5 to about 10.5.

In the practice of the process of this invention the dye concentrate described above is intended to be mixed with a composition containing an oxidizing agent, said composition being hereinafter referred to as the developer. This developer will ordinarily take the form of a liquid vehicle in which the oxidizing agent is distributed or dissolved. Usually the liquid vehicle will be primarily an aqueous vehicle to which, if desired, certain adjuvants may be added.

The oxidizing agent will be selected as the type and concentration so as to perform at least one function, that is to effectively "neutralize" the action of the reducing agent on the hair placed there during the hair waving procedure. Where the dye concentrate employed also contains an oxidation hair dye system the oxidizing agent selection and concentration will be adjusted to take this into account.

The concentration of the oxidizing agent in the developer may vary somewhat. Usually this will amount to about 1% to about 10% by weight of oxidizing agent based on the weight of the developer.

In preparing the second stage neutralizing solution for use in the present process predetermined quantities of the dye concentrate and developer will be mixed together. The proportions in which these components may be mixed to form the second stage neutralizing solution also may vary somewhat. Generally the ratio by weight of dye concentrate to developer will be in the range of from about 0.1 to about 1 parts of dye concentrate per part of developer.

In carrying out the process of this invention the oxidation dye concentrate to which the developer has been added as described above is utilized in the second stage "neutralization" step of a conventional cold permanent hair waving procedure. Generally in the cold permanent waving procedure the hair to be waved is sectioned and the sections are then wound on curlers. It is often advantageous to shampoo the hair prior to winding the hair sections on the curlers. Usually the hair, wound on the rollers is saturated thoroughly with the waving composition, usually in the form of a solution or lotion. Depending on the strength of the waving solutions or lotion and the desired curl tightness, the waving solution or lotion is allowed to remain in contact with the hair for from 2 minutes up to 2 hours. The hair is then rinsed with water and/or towel blotted to remove as much of the remaining waving composition as possible. The hair is then "neutralized" as described in more detail below. This neutralization step is in fact an oxidation reaction which serves to reestablish the disulfide linkages that were broken in the hair keratin molecules during the hair waving procedure.

Neutralization is accomplished in two stages. In the first stage, part of the neutralization is accomplished by means of the developer solution alone and is applied to the hair while the hair is still wrapped on the waving rods. After a period of time, preferably from about 2 to 10 minutes, the composition formed by mixing the developer and the hair dye concentrate is then applied to the hair (which may or may not be on the rods) for a time sufficient to color the hair and to finish the neutralization of the procedure.

The time period during which the second stage neutralization step is carried out may vary somewhat depending upon the results desired. Usually this will be from about 3 to about 20 minutes with the preferred time period being from about 3 to about 7 minutes.

It has also been found that the additional intensification of the dyeout on hair can be produced by incorporating certain metal salts (e.g. salts of Cu, Fe, Al or Zn) preferably in a solution or lotion used to wet the hair before it is wrapped on curlers for the hair waving process. Such salts may include cupric citrate, zinc lactate, aluminum citrate, ferrous sulfate, and the like.

The concentration of the salts contained in the composition used for this purpose can vary. Generally this will be in the range of from about 0.05% to about 2% by weight based on the total weight of these compositions with the preferred range being from about 0.1% to about 0.5% on the same weight basis.

The metal salts moieties can be introduced into hair, in a variety of ways. One of the preferred techniques involves shampooing hair with, for example, a copper salt containing shampoo for about 1 to 2 minutes and then rinsing the hair thoroughly with water, and towel blotting it before wrapping on curlers. The other technique involves contacting the hair with a lotion containing the dissolved metal salt, working the lotion well into the hair and leaving it on for about 1-2 minutes before rinsing and towel-blotting.

The following examples are given to further illustrate the present invention. It is to be understood that the invention is not limited thereto.

The example which follow immediately are illustrative of the process of the present invention when it is used to restore color to the hair that has been previously dyed with an oxidation dye system. In these cases an oxidation dye system is included in the second stage neutralization solution.

Each of the previously dyed hair samples were given a cold hair-waving treatment using as the waving composition either a sulfite based or a thiologlycollic acid based waving solution. The formulas for each of these waving compositions are as follows:

A. Sulfite Waving Composition (SWC)

| Component | % by Wt |
|---|---|
| ammonium bisulfite | 7.5 |
| ammonium hydroxide | 0.9 |
| BRIJ 35 | 0.3 |
| polymethacrylamidopropyltrimethyl ammonium chloride | 1.0 |
| fragrance | 0.2 |
| deionized Water | 90.1 |

B. Thiologlycollic Waving Composition: (TWC)

| Component | % by Wt |
|---|---|
| ammonium thioglycolate | 8.5 |
| ammonium hydroxide | 1.2 |
| Igepal DM 880 | 3.0 |
| EDTA | 0.05 |
| fragrance | 0.95 |
| polymethacrylamidotrimethylammoniumchloride | 1.60 |
| deionized Water | 84.70 |

The waving procedure used to wave the hair differs somewhat with the waving composition that is employed. Thus in case of SWC the shampooed hair was wetted thoroughly with the waving composition prior to winding on rollers. The rolled up hair was then covered with a plastic wrap and left for 60 minutes at room temperature before being rinsed and neutralized. On the other hand, in the case of TWC the shampooed, damp hair was first wound on rollers which are then wetted with a waving composition, covered with a plastic wrap and left for 15 minutes before being rinsed and neutralized.

Following the waving procedure each hair sample was subjected to a first stage neutralization step. The composition used and the procedure employed in the first stage neutralization step are as follows:

C. First Stage Neutralization Composition:

| Component | % by Wt |
|---|---|
| $H_2O_2$ (50%) | 4.2 |
| phosphoric acid | 0.001 |
| styrene/PVP copolymer (clouding agent) | 0.350 |
| water | 95.449 |

D. Procedure for First Stage Neutralization:

With the hair still on rollers the first stage neutralization composition was applied by thoroughly wetting the wrapped hair and gently blotting the excess of the lotion with a paper towel. The time for first stage of neutralization was 3 minutes.

E. Second Stage Neutralization Step

After 3 minutes exposure to the first stage neutralization solution the hair was removed from rollers and the second stage neutralization composition (containing the coloring moieties) was applied by thoroughly wetting the hair and, using both fingers and comb, distributing the above composition uniformly throughout the hair mass. The treatment time in this case was 5 minutes after which time the hair was rinsed and towel blotted.

The second stage neutralization step was formed by mixing 1 part by weight of each of the dye concentrates given below with 1 part of an oxidizing agent solution. The composition of the dye concentrate components employed are as follows:

F.

| Component | % by Wt |
|---|---|
| 4-aminophenol | 0.19 |
| 4-amino-o-cresol | 0.214 |
| oleic acid | 12.00 |
| octoxynol | 9.00 |
| glycerin | 3.50 |
| ammonium hydroxide | 7.00 |
| isopropanol | 8.50 |
| water QS to | 100.0 |

G.

| Component | % by Wt. |
|---|---|
| p-phenylenediamine | 0.1 |
| resorcinol | 0.34 |
| oleic acid | 12.00 |
| octoxynol | 9.00 |
| glycerin | 3.50 |
| ammonium hydroxide | 7.00 |
| isopropanol | 8.50 |
| water QS to | 100.0 |

H.

| Component | % by Wt |
|---|---|
| p-phenylenediamine | 1.55 |
| resorcinol | 0.6 |
| m-aminophenol | 0.55 |
| oleic acid | 12.00 |
| octoxynol | 9.00 |
| glycerin | 3.50 |
| ammonium hydroxide | 7.00 |
| isopropanol | 8.50 |
| water QS to | 100.0 |

The composition of the oxidizing agent solution mixed with each of the aforesaid dye concentrates is as follows:.

| Component | % by Wt |
|---|---|
| $H_2O_2$ (50%) | 4.2 |
| phosphoric Acid | 0.001 |
| styrene/PVP copolymer | 0.350 |
| water | 95.449 |

The curl level of hair samples that was treated in accordance of the process of this invention was observed and recorded.

The curl level was rated on an arbitrary scale of 1 to 5 with 1 being the worst and 5 being best.

Color determinations of the hair dyeings obtained were carried out. This was done using a Hunter-Lab tristimulus colorimeter which can quantify not only the change in color intensity but also the shade shift. To determine the degree, if any, to which there was a change in the color from the original dyed hair sample following treatment according to the process of present invention, the Hunter values and curl level were measured for original dyed hair samples. These were used as a basis for comparison. In addition both the Hunter values and the curl level were measured on hair samples that were subjected to the standard hair waving procedure using the SWC or the TWC.

The results of these tests are summarized in Tables I and II below. In column 2, under "Treatment", a blank space indicates that the hair sample had only been given a preliminary hair dyeing treatment, the shade of the hair sample being given in column 1. Treatment "SWC", or "TWC" designates that the previously dyed hair sample had been subjected to a standard hair waving using SWC or TWC. Treatment "SWC and N&E 110" designates that the previously dyed hair sample was subjected to a hair waving procedure using SWC in which the second neutralization stage is carried out with dye concentrate of a commerical hair dye sold by Clairol, Inc., under the trademark NICE AND EASY, followed by the commercial shade number that has been added to the second stage oxidizing agent solution. The other "Treatments" in column 2 designated by SWC or TWC and a dye concentrate are similar to that described above in connection with "SWC and NE 110" excepting that dye concentrate or the hair waving composition employed will vary as designated by each "Treatment" entry in the Table 1.

The treatment designations in Table II are analogous to these described in Table I with an exception that the dye concentrate used was a commerical hair dye (a mixture of direct and oxidative dyes) sold by Clairol, Inc., under the trademark CHARACTERS.

TABLE I

Effect of Waving w/wo Dyes in the Neutralization Step on Color Changes

| Initial Shade | Treatment | Curl Level* | Hunter Readings** | | | |
|---|---|---|---|---|---|---|
| | | | L | a | b | CD |
| Auburn | | | 26.0 | 9.7 | 10.7 | |
| " | SWC | 5 | 26.4 | 3.9 | 10.0 | 5.81 |
| " | SWC and N&E 110 | 5 | 29.4 | 8.2 | 12.3 | 3.98 |
| " | TWC | 4 | 26.7 | 5.1 | 10.7 | 4.63 |
| " | TWC and N&E 110 | 4 | 26.9 | 9.4 | 11.5 | 1.24 |
| Nat. Brown | | | 26.7 | 2.5 | 9.6 | |
| " | SWC | 5 | 29.3 | 2.6 | 10.6 | 2.74 |
| " | SWC and N&E 116 | 5 | 22.1 | 1.8 | 6.3 | 5.74 |
| " | TWC | 4 | 24.1 | 2.3 | 8.6 | 2.9 |
| " | TWC and N&E 116 | 4 | 22.2 | 1.7 | 6.6 | 5.5 |
| Dark Brown | | | 13.1 | .9 | 1.3 | |
| " | SWC | 5 | 14.1 | 1.5 | 1.8 | 1.3 |
| " | SWC and N&E 120 | 5 | 13.1 | 1.2 | 1.3 | .2 |
| " | TWC | 4 | 12.9 | 1.2 | 1.8 | .6 |
| " | TWC and N&E 120 | 4 | 13.4 | 1.1 | 1.6 | .5 |
| Black | | | 11.9 | .3 | .2 | |
| " | SWC | 5 | 14.9 | 1.4 | 2.6 | 4.0 |
| " | SWC and N&E 122 | 5 | 11.9 | .1 | .1 | .2 |
| " | TWC | 4 | 11.8 | .8 | .7 | .7 |
| " | TWC and N&E 122 | 4 | 11.0 | .1 | .5 | .9 |

TABLE II

Effect of Waving w/wo Dyes in the Neutralization Step on Color Changes

| Initial Shade | Treatment | Curl Level* | Hunter Readings** | | | |
|---|---|---|---|---|---|---|
| | | | L | a | b | CD |
| Auburn | — | — | 24.3 | 7.6 | 9.4 | — |
| " | TWC | 4 | 28.8 | 4.3 | 9.1 | 5.53 |
| " | TWC + Characters Red | 4 | 24.4 | 6.9 | 9.2 | 0.65 |
| Medium Brown | — | | 15.6 | 1.4 | 4.5 | |
| " | TWC | 4 | 16.6 | 1.4 | 4.5 | 1.04 |
| " | TWC + Characters Violet | 4 | 15.6 | 1.5 | 4.2 | 0.37 |

*Curl Level ranking: 5 - best, 1 - worst
**Hunter tristimulus readings are given in terms of overall intensity (L values); redness of the shade (a values); and its yellowness (b values). CD is the overall color difference calculated from L, a, and b values.

The data strongly suggest, and visual observations confirm that the process of this invention can be used effectively either in color restoration (using dye formulas N&E 110, N&E 120 and N&E 122 or Characters) or in color build-up (using dye formulas N&E 110 and N&E 116). The end results depend on the concentration and dye moiety employed.

We claim:

1. In a process for simultaneously cold waving and coloring hair in which the hair is first treated with a hair waving composition containing a reducing agent wrapped in rods, and thereafter treated with a neutralization composition containing an oxidizing agent, the improvement which comprises carrying out said prior to the start of the second stage, the first stage comprising treating the hair with a first stage neutralization composition containing an oxidizing agent for 2 to 10 minutes to partially neutralize the reducing on the hair, and the second stage comprising treating the hair with a second stage neutralization composition containing an oxidizing agent and hair dye for 3 to 7 minutes to complete the neutralization and to simultaneously dye the hair.

2. The process of claim 1 wherein said reducing agent is selected from the group consisting of sulfites, thioglycolic acids and salts thereof.

3. The process of claim 2 wherein the concentration of reducing agent in said hair waving composition is from about 2% to about 15% by weight based on the total weight of said hair waving composition.

4. The process of claim 1 wherein said hair dye is a direct dye.

5. The process of claim 1 wherein said hair dye comprises an oxidation hair dye system containing a primary oxidation hair dye intermediate and an oxidation hair dye coupler.

6. The process of claim 1 or 5 wherein said oxidizing agent is an aqueous hydrogen peroxide solution.

7. The process of claim 6 wherein the concentration of the oxidizing agent in the first stage neutralization composition is from about 1% to about 15% by weight based on the total weight of said composition and the concentration of the oxidizing agent in the second stage neutralization composition is from about 2% to about 4% by weight based on the total weight of said composition.

8. The process of claim 7 wherein the hair dye is present in the second stage neutralization composition in an amount of from about 0.02% to about 4% by weight based on the total weight of said composition.

9. The process of claim 1 further comprising the step of contacting the hair with a metal salt solution following treatment with the hair waving composition and prior to treatment with the first stage neutralization composition.

10. The process of claim 1 wherein the salt solution contains a cation selected from $Cu^{++}$, $Fe^{++}$ in an amount of from about 0.05% to about 2% by weight based on the total weight of the salt solution.

* * * * *